United States Patent
Smith et al.

(10) Patent No.: US 12,178,586 B2
(45) Date of Patent: *Dec. 31, 2024

(54) PREDICTIVE QRS DETECTION AND R-TO-R TIMING SYSTEMS AND METHODS

(71) Applicants: NuPulseCV, Inc., Raleigh, NC (US); North Carolina State University, Raleigh, NC (US)

(72) Inventors: Robert M. Smith, Raleigh, NC (US); Nagarjuna Reddy Chinta, Apex, NC (US); Ryan Daniel McCormick, Durham, NC (US); Douglas Edward Ivers, Cary, NC (US); Cranos M. Williams, Raleigh, NC (US); Divyakumar Mahiman Badheka, Raleigh, NC (US); Hubert Troy Nagle, Jr., Durham, NC (US); Sai Bhargav Dasari, Raleigh, NC (US); Shamim Samadi, San Jose, CA (US)

(73) Assignees: NuPulseCV, Inc., Raleigh, NC (US); North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/707,424

(22) Filed: Mar. 29, 2022

(65) Prior Publication Data
US 2022/0288380 A1    Sep. 15, 2022

Related U.S. Application Data

(63) Continuation of application No. 16/401,368, filed on May 2, 2019, now Pat. No. 11,285,313.

(51) Int. Cl.
*A61B 5/352*  (2021.01)
*A61B 5/346*  (2021.01)
(Continued)

(52) U.S. Cl.
CPC .............. *A61B 5/346* (2021.01); *A61B 5/347* (2021.01); *A61B 5/352* (2021.01); *A61M 60/135* (2021.01);
(Continued)

(58) Field of Classification Search
CPC ... A61M 60/50; A61M 2230/06; A61B 5/316; A61B 5/352; A61B 5/726
See application file for complete search history.

(56) References Cited

U.S. PATENT DOCUMENTS

| 4,692,148 A | 9/1987 | Kantrowitz |
| 4,697,574 A | 10/1987 | Karcher |

(Continued)

FOREIGN PATENT DOCUMENTS

| JP | 2009082664 A | 4/2009 |
| JP | 2018161324 A | 10/2018 |

(Continued)

OTHER PUBLICATIONS

Bouaziz, F., Boutana, D., & Benidir, M. (2014). Multiresolution wavelet-based QRS complex detection algorithm suited to several abnormal morphologies. IET Signal Processing, 8(7), 774-782. https://doi.org/10.1049/iet-spr.2013.0391 (Year: 2014).*

(Continued)

*Primary Examiner* — Lynsey C Eiseman
*Assistant Examiner* — Skylar Lindsey Christianson
(74) *Attorney, Agent, or Firm* — LOEB & LOEB LLP

(57) ABSTRACT

The present disclosure is directed towards systems and methods built for predictively timing the inflation and/or deflation of an intra-aortic balloon pump. A controller operates in three states: (1) initialization state, (2) learning state, and (3) peak detection state. The controller decomposes a patient's electrocardiogram signal to a power signal. It then learns characteristics of the patient's electrocardiogram sig- (Continued)

nal during the learning state and computes adaptive threshold parameter values. During the peak detection state, the controller applies the learnt threshold parameter values on a current electrocardiogram signal to identify occurrence and timings of R peaks in the electrocardiogram signal. The R-to-R peak timings are then used to trigger inflation of an intra-aortic balloon pump.

18 Claims, 16 Drawing Sheets

(51) Int. Cl.
| | |
|---|---|
| A61B 5/347 | (2021.01) |
| A61M 60/135 | (2021.01) |
| A61M 60/139 | (2021.01) |
| A61M 60/295 | (2021.01) |
| A61M 60/50 | (2021.01) |
| A61M 60/515 | (2021.01) |
| A61M 60/843 | (2021.01) |
| A61B 5/00 | (2006.01) |

(52) U.S. Cl.
CPC ........ *A61M 60/139* (2021.01); *A61M 60/295* (2021.01); *A61M 60/50* (2021.01); *A61M 60/515* (2021.01); *A61M 60/843* (2021.01); *A61B 5/726* (2013.01); *A61M 2230/06* (2013.01)

(56) References Cited

U.S. PATENT DOCUMENTS

| | | | |
|---|---|---|---|
| 4,809,681 A | 3/1989 | Kantrowitz | |
| 5,169,379 A | 12/1992 | Freed | |
| 5,365,933 A | 11/1994 | Elghazzawi | |
| 6,050,932 A | 4/2000 | Franchi | |
| 6,132,363 A | 10/2000 | Freed | |
| 6,179,793 B1 | 1/2001 | Rothman | |
| 6,290,641 B1 | 9/2001 | Nigroni | |
| 6,511,412 B1 | 1/2003 | Freed | |
| 6,679,829 B2 | 1/2004 | Nigroni | |
| 7,169,109 B2 | 1/2007 | Jansen | |
| 7,250,025 B2 | 7/2007 | Nigroni | |
| 7,343,198 B2 | 3/2008 | Behbehani | |
| 7,513,864 B2 | 4/2009 | Kantrowitz | |
| 7,751,873 B2 | 7/2010 | De Voir | |
| 8,016,738 B2 | 9/2011 | Hanlon-Pena | |
| 8,066,628 B1* | 11/2011 | Jeevanandam | A61M 60/497 600/17 |
| 8,204,582 B2 | 6/2012 | Zantos | |
| 8,540,618 B2 | 9/2013 | Kantrowski | |
| 9,265,871 B2 | 2/2016 | Jeevanandam | |
| 9,451,920 B2 | 9/2016 | Khair | |
| 9,694,122 B2 | 7/2017 | Smith | |
| 10,137,230 B2 | 11/2018 | Novack | |
| 11,285,313 B2 | 3/2022 | Smith | |
| 2001/0034469 A1 | 10/2001 | Nigroni | |
| 2003/0074144 A1 | 4/2003 | Freed | |
| 2004/0039292 A1* | 2/2004 | Schlegel | A61B 5/366 600/509 |
| 2004/0049120 A1 | 3/2004 | Cao | |
| 2006/0041201 A1 | 2/2006 | Behbehani | |
| 2007/0161916 A1 | 7/2007 | Zantos | |
| 2007/0197926 A1 | 8/2007 | Danehorn | |
| 2013/0274616 A1 | 10/2013 | Bhatkar | |
| 2014/0277241 A1 | 9/2014 | Bleich | |
| 2015/0018632 A1 | 1/2015 | Khair | |
| 2015/0223759 A1* | 8/2015 | Ong | A61B 5/14542 600/301 |
| 2017/0216506 A1* | 8/2017 | Jeevanandam | A61M 60/497 |
| 2018/0028085 A1 | 2/2018 | Zhang | |
| 2018/0104491 A1 | 4/2018 | Lerner | |
| 2018/0350468 A1* | 12/2018 | Friedman | A61B 5/14546 |
| 2019/0246925 A1 | 8/2019 | Fecteau | |
| 2020/0345910 A1 | 11/2020 | Smith | |

FOREIGN PATENT DOCUMENTS

| | | |
|---|---|---|
| JP | 2018538120 A | 12/2018 |
| WO | 2013180286 | 12/2013 |

OTHER PUBLICATIONS

The International Search Report, dated Jun. 26, 2020, mailing date Jul. 10, 2020 in connection with PCT International Application No. PCT/US2020/030803, 3 pages.

The International Search Report, dated Jun. 26, 2020, mailing date of Sep. 7, 2020 in connection with PCT International Application No. PCT/2020/030797, 9 pages.

Bouaziz, Fatiha, Multiresolution wavelet-based QRS complex detection algorithm suited to several abnormal morphologies, 2014, IET Signal Processing, vol. 8—Issue7, pp. 774-782 (Year: 2014).

Notice of Allowance dated Aug. 11, 2021 for U.S. Appl. No. 16/401,368 (pp. 1-8).

Notice of Allowance dated Nov. 22, 2021 for U.S. Appl. No. 16/401,368 (pp. 1-9).

Office Action dated Jun. 23, 2021 for U.S. Appl. No. 16/401,407 (pp. 1-8).

Z. El-Ghazzawi, J. Cooper, P. Ford, Z. Ladin and J. Welch, "An algorithm to extract blood-pressure waveform features during intra-aortic balloon pump assist," Images of the Twenty-First Century. Proceedings of the Annual International Engineering in Medicine and Biology Society, Seattle, WA, USA, 1989.

EPO Communication pursuant to Article 94(3) issued in App. No. EP20726660, dated Jun. 30, 2023, 6 pages.

\* cited by examiner

PRIOR-ART

PREDICTIVE QRS DETECTION AND R-TO-R TIMING SYSTEMS AND METHODS

BACKGROUND

The invention relates generally to medical devices, and more particularly to systems and methods related to the operation of medical devices, such as intra-aortic balloon pumps, based on physiological measurements. About 5.7 million adults in the United States have heart failure, according to the U.S. Centers for Disease Control and Prevention website. Each year, about 100,000 people nationally are diagnosed with advanced heart failure and require some sort of mechanical support, such as intra-aortic balloon pumps. The balloon pump is positioned inside the aorta, typically in the proximal descending aorta. The balloon pump (typically 40-50 milliliters in capacity) is inflated and deflated in time with the contraction of the left ventricle. During diastole, the balloon is inflated, thereby driving blood in the ascending aorta and aortic arch into the coronary arteries to supply oxygen to the heart muscle. During systole, as the left ventricle contracts, the balloon is deflated so as to decrease the afterload. This procedure is termed "counterpulsation."

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Figure 1A:
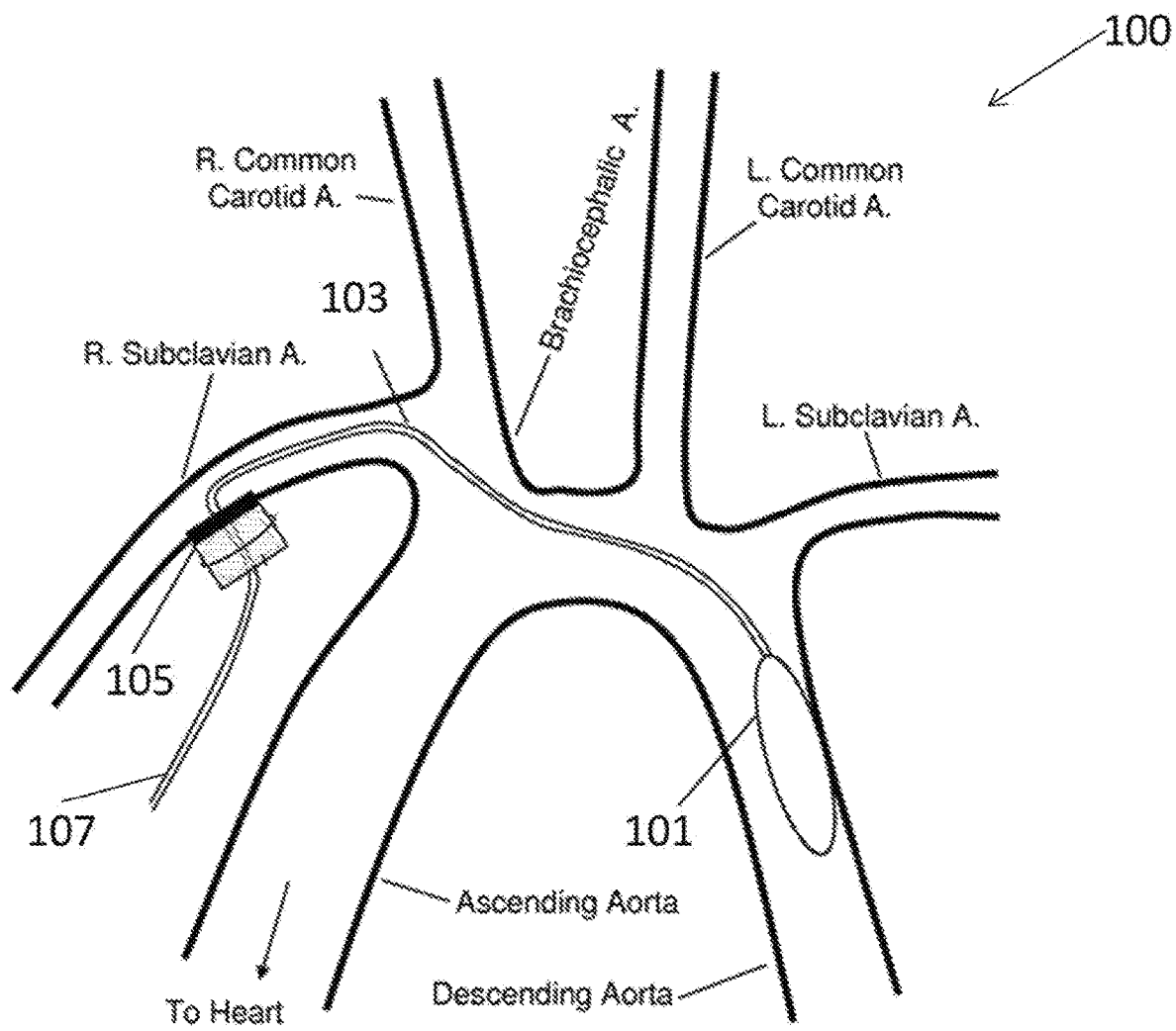
FIGS. 1A and 1B illustrate an intra-aortic balloon pump in accordance with some embodiments.

Intra-aortic balloon pump devices typically process ECG signals for efficient and optimum operation. One of the most important parts of ECG signal processing and intra-aortic balloon pump operation is interpretation of QRS complex and obtaining its characteristics. The QRS complex is a name for the combination of three of the graphical deflections seen on a typical electrocardiogram. In adults, the QRS complex normally lasts 0.06-0.10 seconds; in children and during physical activity, it may be shorter. The Q, R, and S waves occur in rapid succession, do not all appear in all leads, and reflect a single event and thus are usually considered together. A Q wave is any downward deflection immediately following the P wave. An R wave follows as an upward deflection, and the S wave is any downward deflection after the R wave. The T wave follows the S wave, and in some cases, an additional U wave follows the T wave.

R wave is one of the most important sections of this complex, which has an essential role in diagnosis of heart rhythm irregularities and also in determining heart rate variability (HRV). Traditional systems for detecting QRS complex include differentiation methods, digital filters, neural networks, filter banks, hidden Markov models, genetic algorithm, and maximum a posteriori (MAP) estimator. These methods are highly sensitive to noise and generally cause errors in detecting the correct timing of R waves in ECG signals. As a result, conventional systems and methods for intra-aortic balloon pumps suffer from an inability to predictively time the inflation and/or deflation of the balloon pump.

In view of the shortcomings of conventional approaches to accurately detecting the occurrence and timing R waves, the inventors have recognized that a new approach to predicting R wave and R peak timings that is more accurate, reliable, and efficient would have significant utility.

A software, hardware, and/or firmware facility ("the facility") that provides a solution to predictively time the occurrence of future R peaks to efficiently inflate and/or deflate an intra-aortic balloon pump is described. In several embodiments, the facility operates as a state machine comprising three states: (1) initialization state, (2) learning state, and (3) peak detection state. By performing in some or all of the manners discussed below, the facility improves the prediction of future R-peaks so that a corresponding intra-aortic balloon pump is inflated and/or deflated in an efficient and reliable manner. This results in an improved patient care experience that keeps a patient's heart pumping in a closely natural rhythm. The facility described herein for QRS detection and/or R-to-R timing may be used for various devices including, but not limited to pacemakers, heart monitors, defibrillators, heartrate monitors, smart watches, athletic accessories, and the like.

DESCRIPTION OF FIGURES

The following description provides certain specific details of the illustrated examples. One skilled in the relevant art will understand, however, that embodiments can be practiced without many of these details. Likewise, one skilled in the relevant art will also understand that the present disclosure can include many other features not described in detail herein. Additionally, some well-known structures or functions may not be shown or described in detail below, to avoid unnecessarily obscuring the relevant descriptions of the various examples.

Figure 1B:
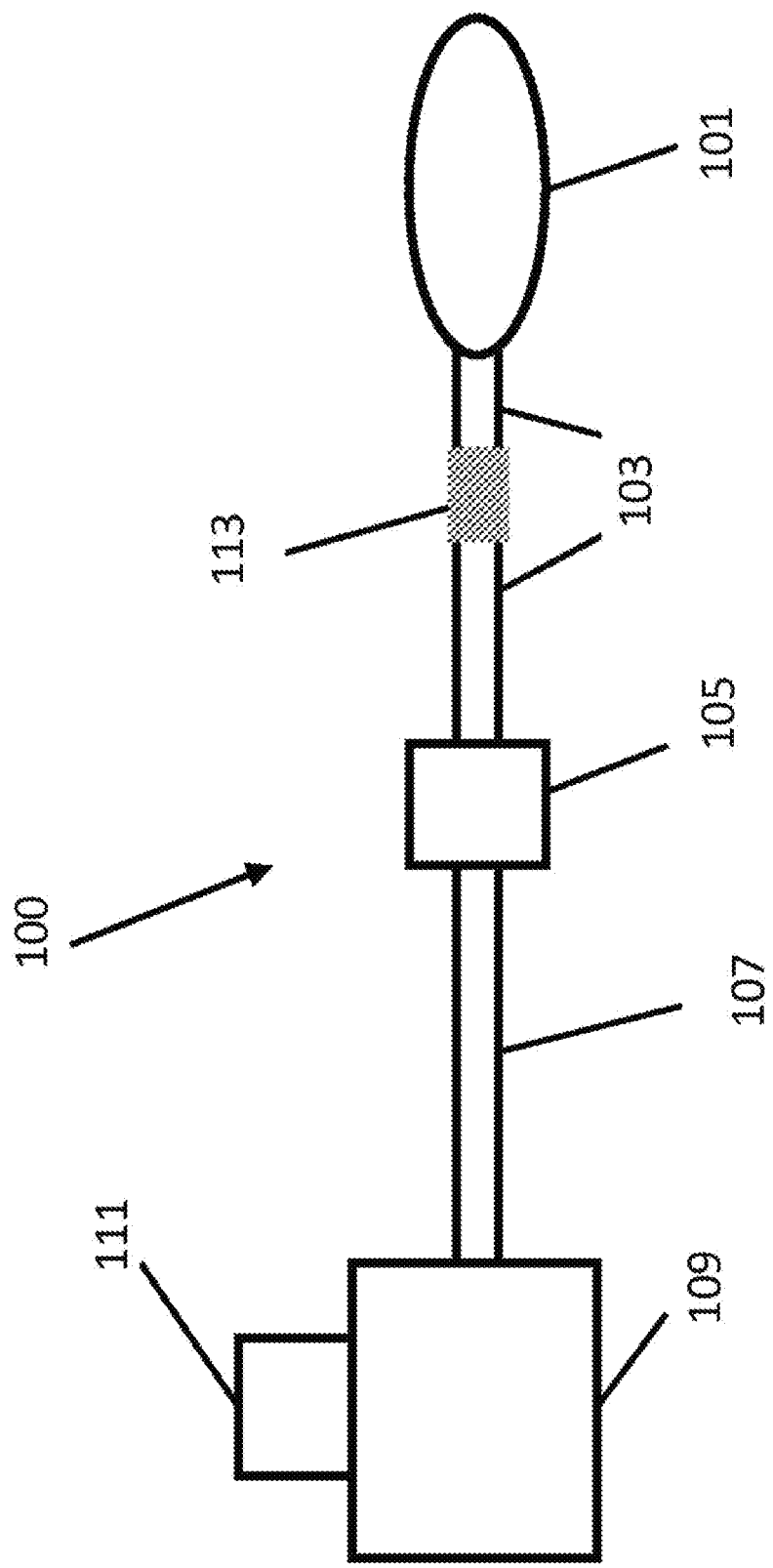

Several implementations are discussed below in more detail in reference to the figures. Turning now to the figures, FIGS. 1A and 1B illustrate an example of an intra-aortic balloon pump facility 100. The intra-aortic balloon pump 100 may be sized and shaped to dangle inside a patient's aorta. The intra-aortic balloon pump 100 may include a balloon 101 that is configurably connected to an internal drive line 103 that connects to a skin interface device 105. As illustrated in FIG. 1B, an external drive line 107 may connect the skin interface device 105 to a driver 109.

At its proximal end, balloon 101 is connected to the distal end of the internal drive line 103. The skin interface device 105 connects the proximal end of the internal drive line 103 to the distal end of the external drive line 107. The proximal end of the external drive line 107 is connected to the driver 109. The driver 109 may comprise or be connected to a controller 111. An arterial interface 113 may be sized and shaped to pass the internal drive line 103 through an arterial wall.

In several embodiments, the intra-aortic balloon pump 100 may include a controller 111 configured in accordance with the systems and methods described herein. The controller 111 may control the operation of the valves and bellows (not shown) of the driver 109 to control the flow of a pumping medium (for example, air) and the inflation and deflation of the balloon 101. The controller 111 may receive one or more signals from the balloon 101 and surrounding areas. Signals may include those received from electrodes, pressure sensors and the like (for example, electrocardiogram signals). In several embodiments, the controller 111 receives one or more of the following data values about a patient from, for example, the skin interface device 105: patient identifier (for example, a unique patient identification alphanumeric string), name of the patient, age of the patient, average heart rate of the patient, maximum heart rate of the patient, minimum heart rate of the patient, pulse of the patient, average R-to-R time interval of the patient, maximum R-to-R time interval of the patient, minimum R-to-R time interval of the patient, average R-peak of the patient, maximum R-peak of the patient, minimum R-peak of the patient, and so on. In several embodiments, controller 111 retrieves and/or computes one or more of the above listed data values based on a subset of the received information about the patient. For example, based on a patient identifier, controller 111 retrieves the following data values (from, for example, a communicatively connected memory): name of the patient, average heart rate of the patient, pulse of the patient, and average R-to-R time interval of the patient.

Figure 2:
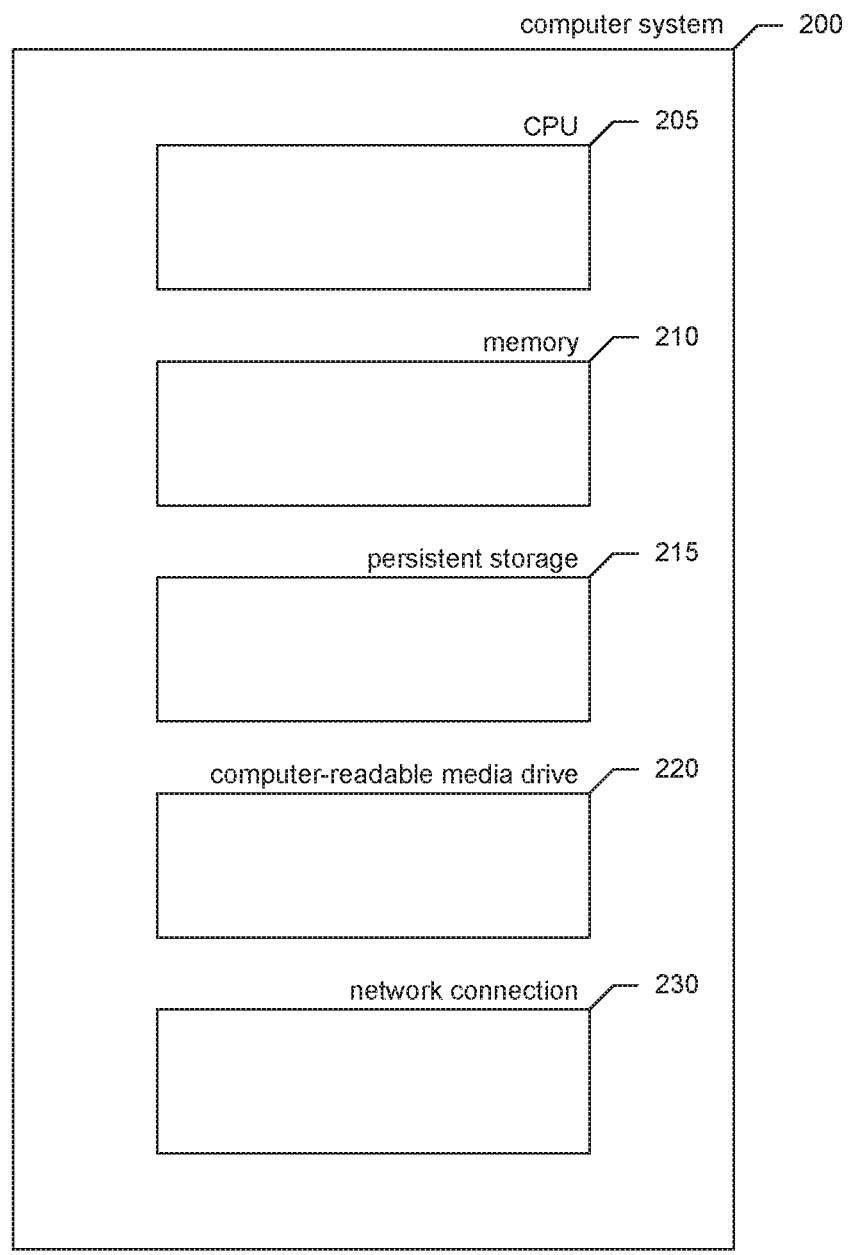
FIG. 2 is a block diagram showing some of the components typically incorporated in a controller in accordance with some embodiments.

FIG. 2 is a block diagram showing some of the components typically incorporated in controller 111. In various embodiments, the controller 111 includes zero or more of each of the following: a central processing unit ("CPU") 205 for executing computer programs; a computer memory 210 for storing programs and data while they are being used, including the facility and associated data, an operating system including a kernel, and device drivers; a persistent storage device 215, such as a hard drive or flash drive for persistently storing programs and data (for example, patient related data); a computer-readable media drive 220, such as a floppy, CD-ROM, or DVD drive, for reading programs and data stored on a computer-readable medium; and a network connection 230 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. For example, via the network connection 230, controller 111 can retrieve patient related data from a remote data storage location (for example, a cloud data storage location). While computer systems configured as described above are typically used to support the operation of the controller 111, those skilled in the art will appreciate that the facility may be implemented using devices of various types and configurations, and having various components.

Figure 3A:
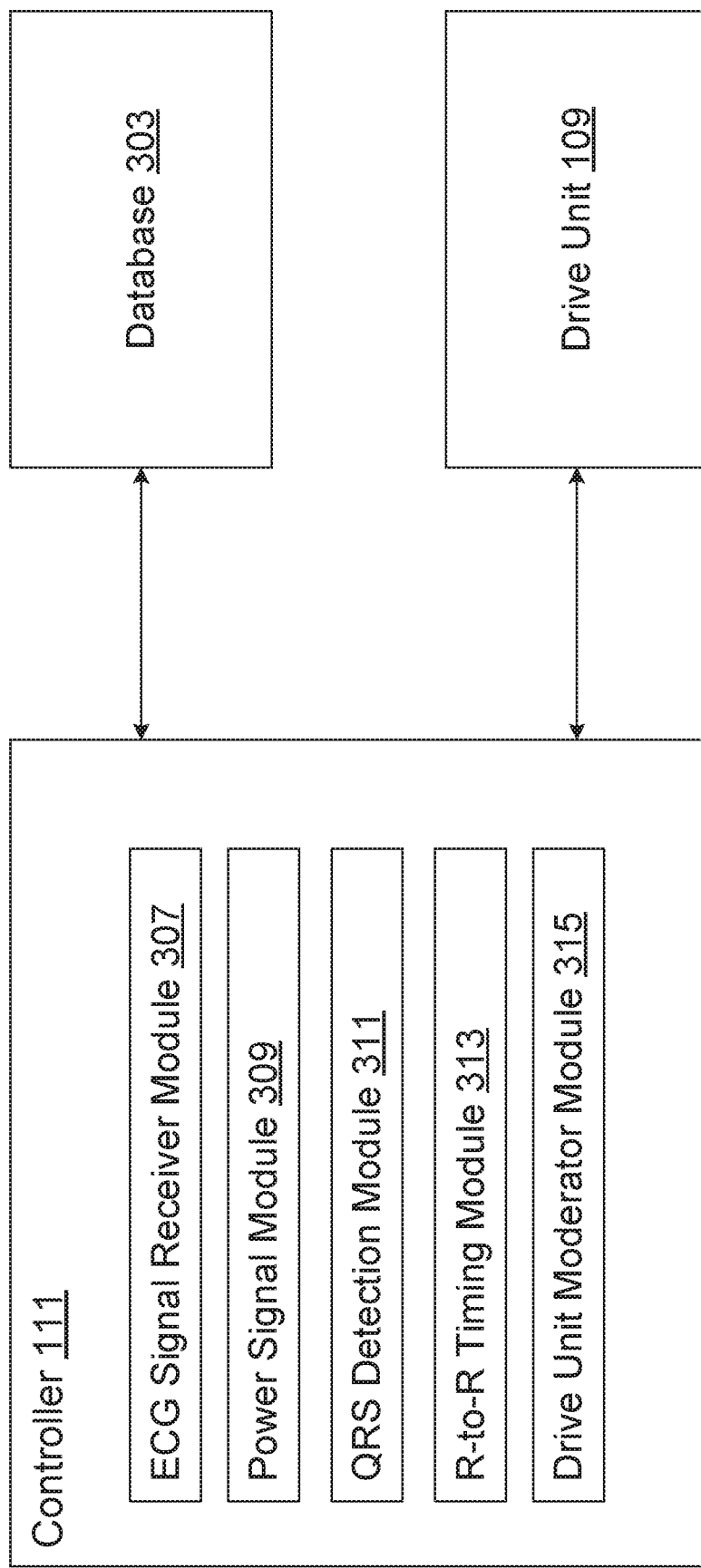
FIG. 3A illustrates components of a controller in accordance with some embodiments.
Figure 3B:
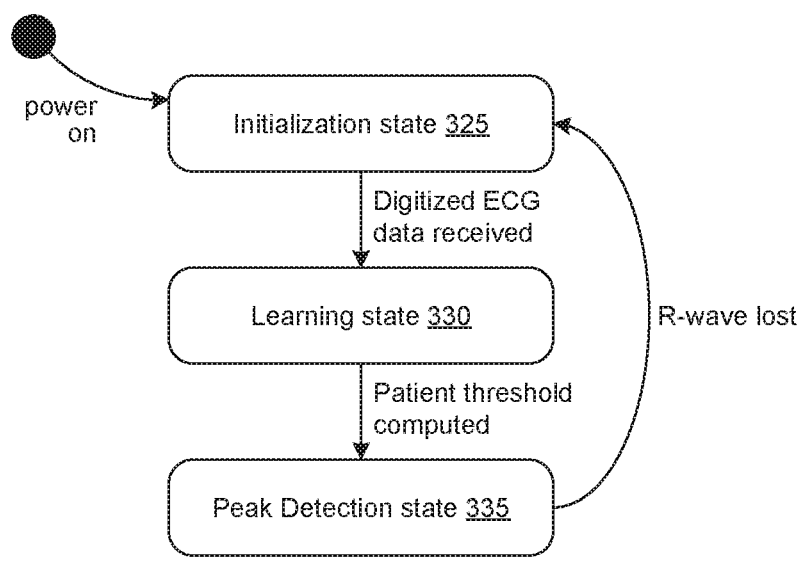
FIG. 3B illustrates a state diagram of the controller in accordance with some embodiments.

FIG. 3A illustrates components of a controller in accordance with some embodiments. In some embodiments, the controller may be configured to be on a drive unit for an intra-aortic balloon pump and configurably connected to a database 303. Controller 111 may include signal receiver module 307, power signal module 309, QRS detection module 311, R-to-R timing module 313, and drive unit moderator module 315. In several embodiments, the controller operates as a state machine comprising three states as depicted in FIG. 3B: (1) initialization state 325, (2) learning state 330, and (3) peak detection state 335.

Initialization State

Figure 4A:
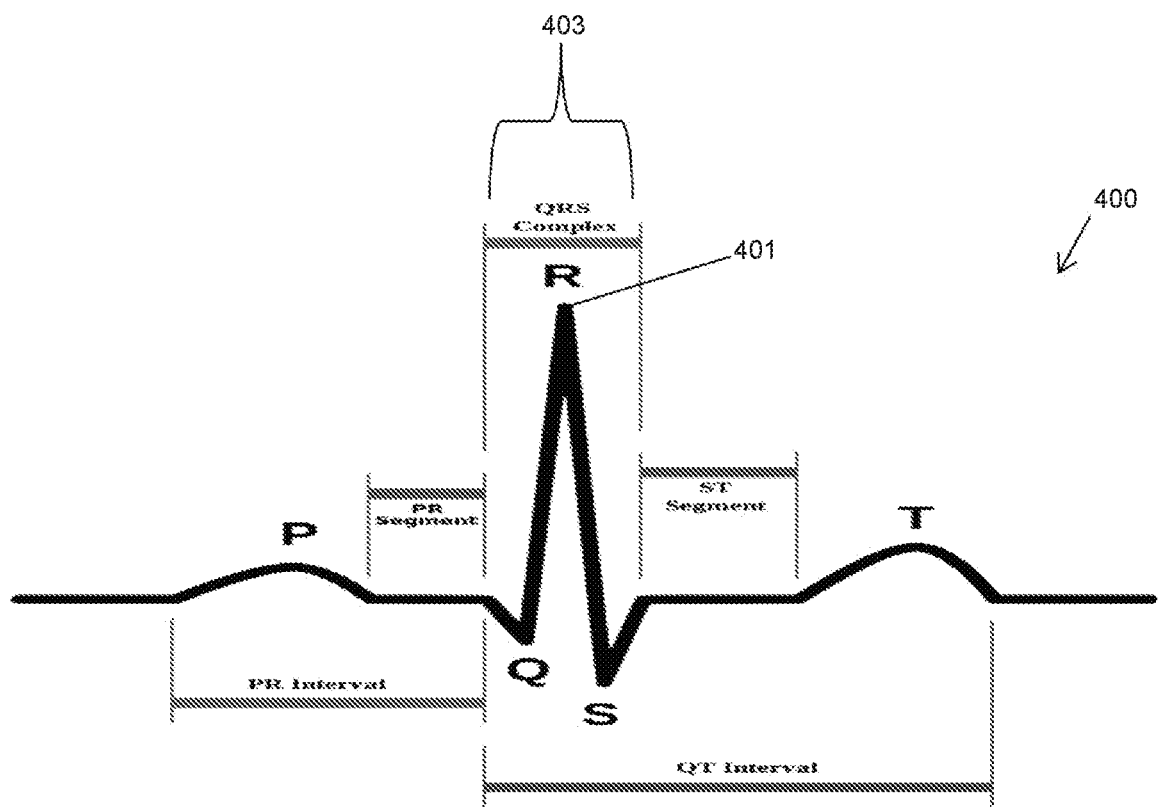
FIG. 4A illustrates a QRS complex in an electrocardiogram signal in accordance with some embodiments.

The signal receiver module 307 of the controller may be configured to receive a signal (for example, analog electrocardiogram signal). For example, the controller receives an electrocardiogram signal from remote devices (for example, one or more skin interface devices (SID) implanted in a patient's body). Applicants' U.S. Pat. Nos. 9,265,871 and 10,137,230 provide more details regarding suitable SIDs and are incorporated by reference herein in their entireties. In several embodiments, the signal receiver module 307 digitizes the received electrocardiogram signal and/or applies one or more filters to obtain a filtered electrocardiogram signal that is suitable for further processing by the facility. Example filters may include, but are not limited to, bandpass filters, derivative filters, squaring filters, and/or applying moving window integrals. FIG. 4A illustrates a portion of an electrocardiogram signal 400 (including a QRS complex 403) in accordance with some embodiments. A QRS complex 403 is a feature of the electrocardiogram signal indicative of depolarization of a heart. An R-peak 401 is an element within the QRS complex 403. Real-time detection of these peaks requires an appropriate threshold that is capable of differentiating between significant peaks, which typically denote the QRS complex, and minor peaks which may be associated with noise, T waves, or P waves. The facility described herein is configured to accurately detect and predict QRS complexes and R-peaks. During the initialization state 325, the controller receives the electrocardiogram signal data and initializes one or more variables, buffers, memory, and the like. For example, the controller receives a patient identifier (for example, a unique patient identification alphanumeric string) to initialize values of one or more of the following variables: name of the patient, age of the patient, average heart rate of the patient, maximum heart rate of the patient, minimum heart rate of the patient, pulse of the patient, average R-to-R time interval of the patient, maximum R-to-R time interval of the patient, minimum R-to-R time interval of the patient, average R-peak of the patient, maximum R-peak of the patient, minimum R-peak of the patient, and so on.

Learning State

Figure 4B:
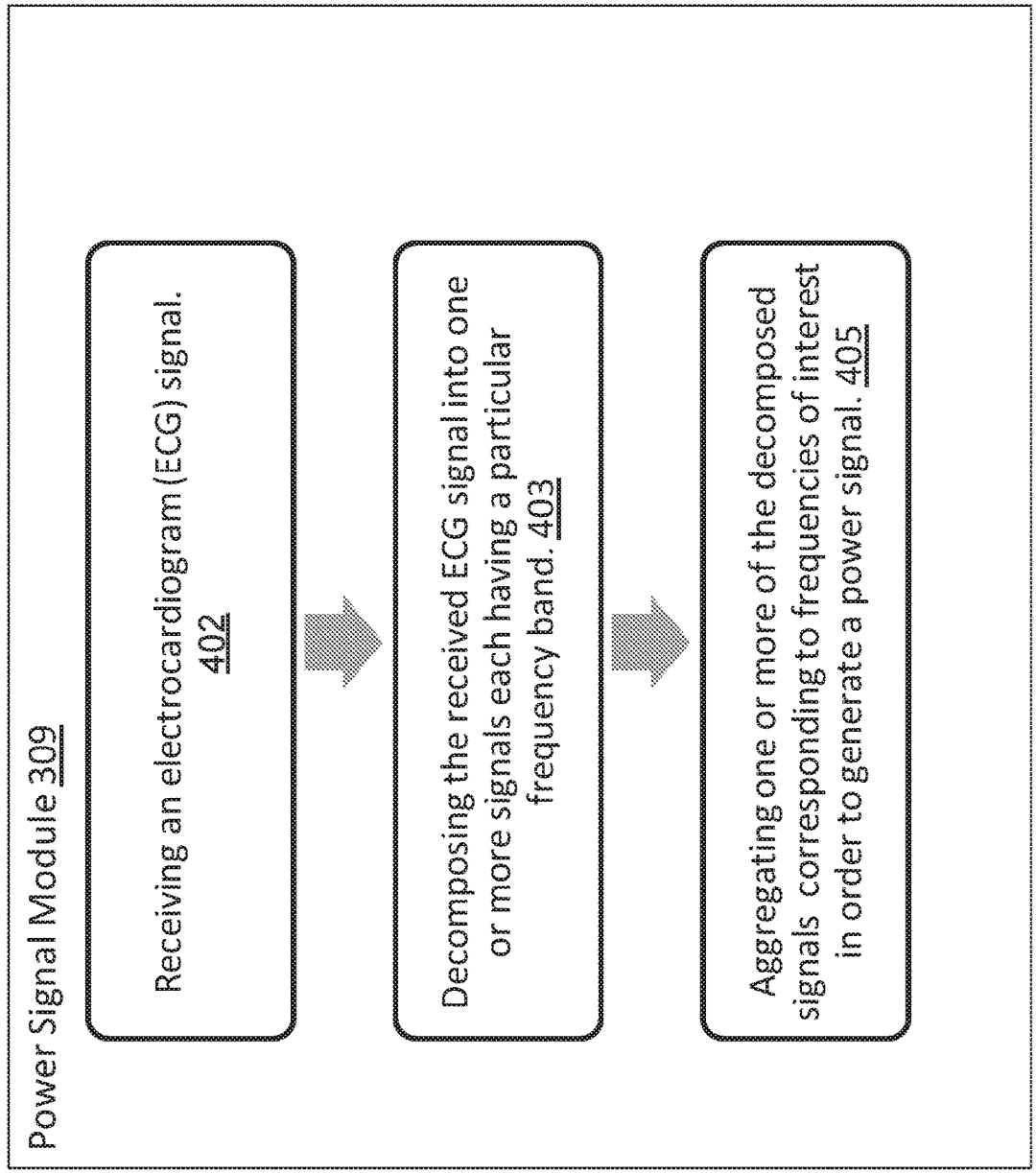
FIG. 4B is a flow diagram illustrating a method performed by a power signal module of a controller in accordance with some embodiments.
Figure 4C:
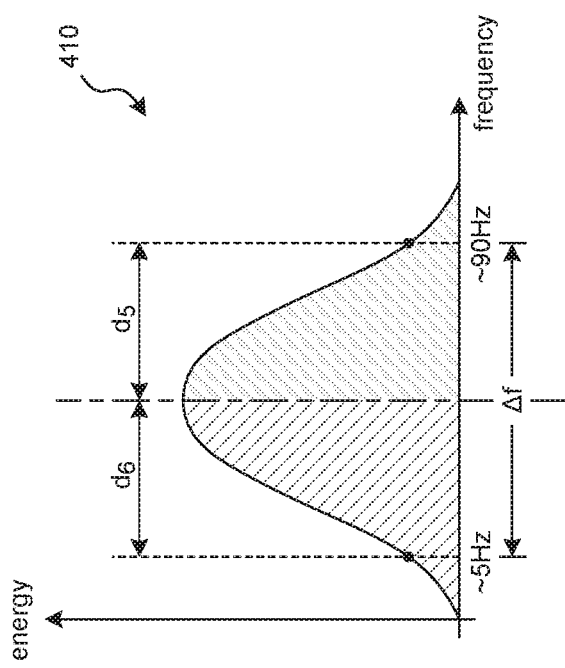
FIGS. 4C and 4D illustrate an electrocardiogram signal received and processed in accordance with some embodiments.
Figure 4D:
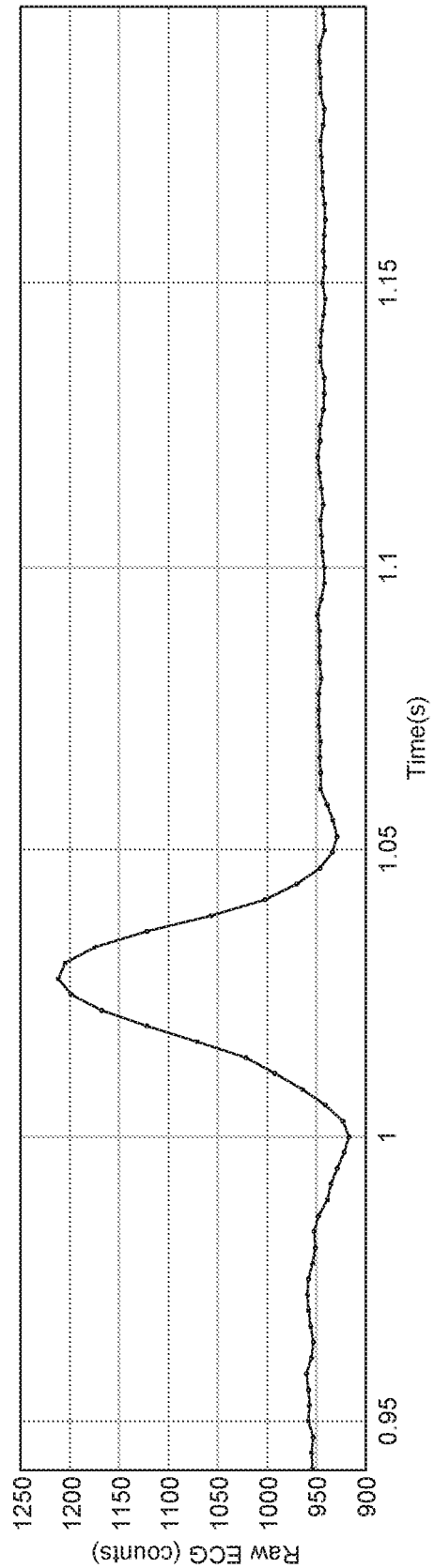

After completing the initialization state 325, the controller enters the learning state 330. During the learning state 330, the controller generates a first power spectrum signal by decomposing the received first electrocardiogram signal (for example, using historical electrocardiogram signal for a patient). The power signal module 309 in the controller is configured to generate a power signal based on the digitized and/or filtered electrocardiogram signal. FIG. 4B is a flow diagram illustrating a method performed by the power signal module 309 of the controller 111 in accordance with several embodiments. The method includes the acts of receiving an electrocardiogram (ECG) signal 400 (act 402). FIGS. 4C and 4D illustrate portions of electrocardiogram signals 410 and 415 received and processed in accordance with some embodiments. At act 404, the power signal module 309 may decompose the received electrocardiogram signal into one or more sub-bands or frequencies of interest. At act 405, the power signal module 309 may then aggregate one or more sub-bands of interest to generate the power signal. The one or more sub-bands of interest may be selected based on characteristics of the received signal, such as the number of received information vectors, number of electrode leads used to capture the electrocardiogram signal, location of electrode leads used to capture the electrocardiogram signal, and so on.

Figure 4E:
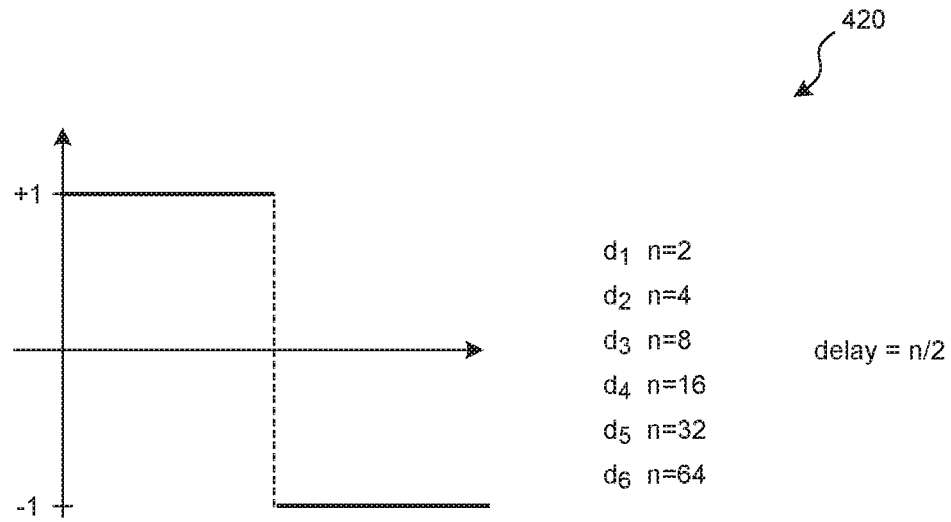
FIG. 4E illustrates a transformation signal in accordance with some embodiments.
Figure 4F:
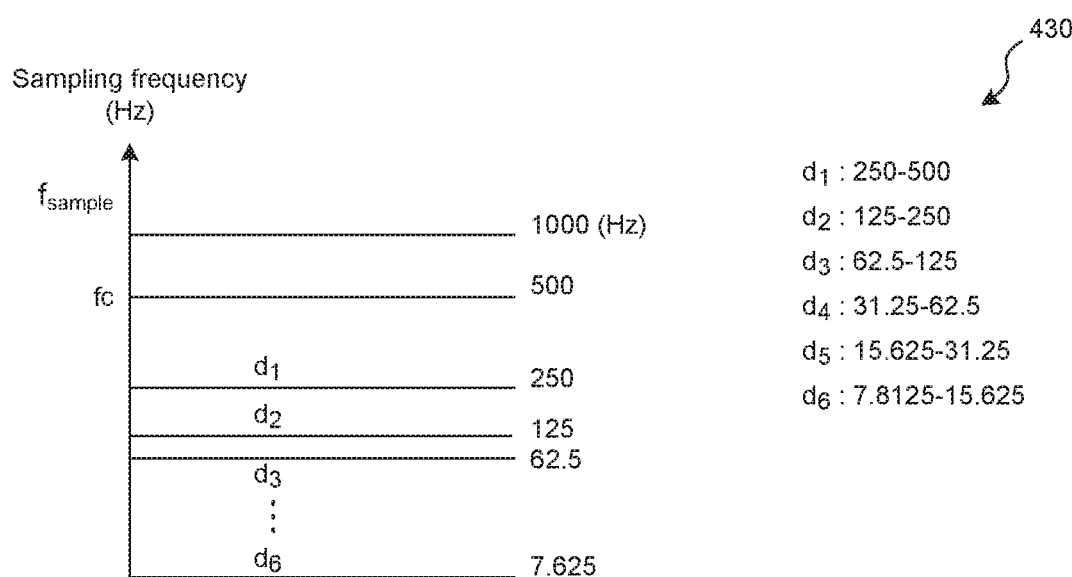
FIGS. 4F and 4G illustrate decomposed electrocardiogram signals in accordance with some embodiments.
Figure 4G:
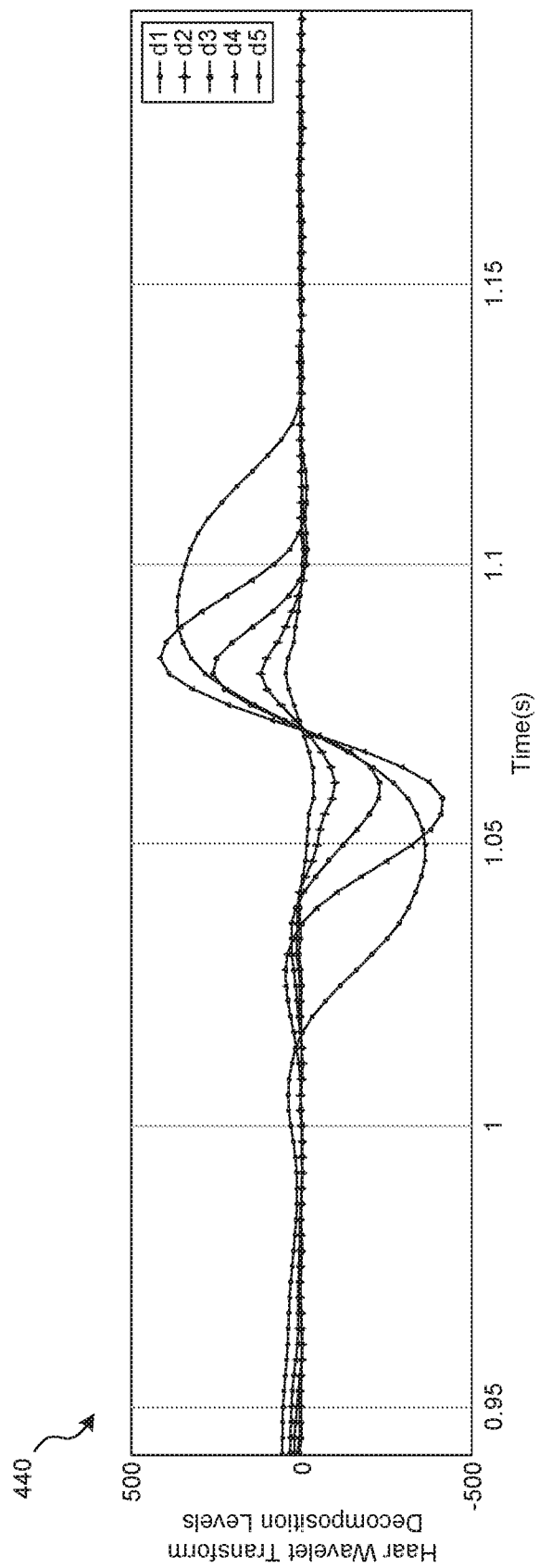

As an illustrative example, the facility collects electrocardiogram signal data using three electrode leads (corresponding to three vectors each) and chooses data from one of the electrode leads (corresponding to one of the three vectors) for monitoring at 1000 Hz sampling. The power signal module 309 applies a transformation signal (for example, a Haar wavelet 420 illustrated in FIG. 4E) to decompose the electrocardiogram signal from the selected electrode lead into discrete frequency signals. For example, FIGS. 4F and 4G illustrate decomposed electrocardiogram signals 430 and 440 in accordance with some embodiments. The power signal module 309 then selects the following sub-bands of interest: a first portion in the d5 frequency range (15.625 Hz to 31.25 Hz) and a second portion in the d6 frequency range (7.8125 Hz to 15.625 Hz). The power signal module 309 aligns the selected portions in the d5 and d6 frequency range to compute the power signal ("h-signal") =|d5.d6|.

In several embodiments, the facility collects electrocardiogram signal data using three (or more) electrode leads (corresponding to three (or more) vectors each) and chooses data from all three electrode leads (all three vectors) for monitoring at 500 Hz sampling. After applying the Haar wavelet transform on the electrocardiogram data, the power signal module 309 selects the following sub-bands of interest from the vector with the best signal characteristics: a first portion in the d4 frequency range (31.25 Hz to 62.5 Hz) and a second portion in the d5 frequency range (15.625 Hz to 31.25 Hz). The delay in detecting and processing the electrocardiogram data is a direct function of the number of electrodes (or vectors) whose data is utilized (delay=n/2, where n is a function of the number of the higher frequency band). For example, when data from a single electrode (and a single vector) is used by the power signal module 309 so that the higher frequency band selected is d6, the amount of delay=32 seconds $$\left(\frac{2^6}{2}\right).$$

similarly, when data from three electrodes (and three vectors) is used by the power signal module 309 so that the higher frequency band selected is 5, the amount of delay=16 seconds $$\left(\frac{2^5}{2}\right).$$

Figure 4H:
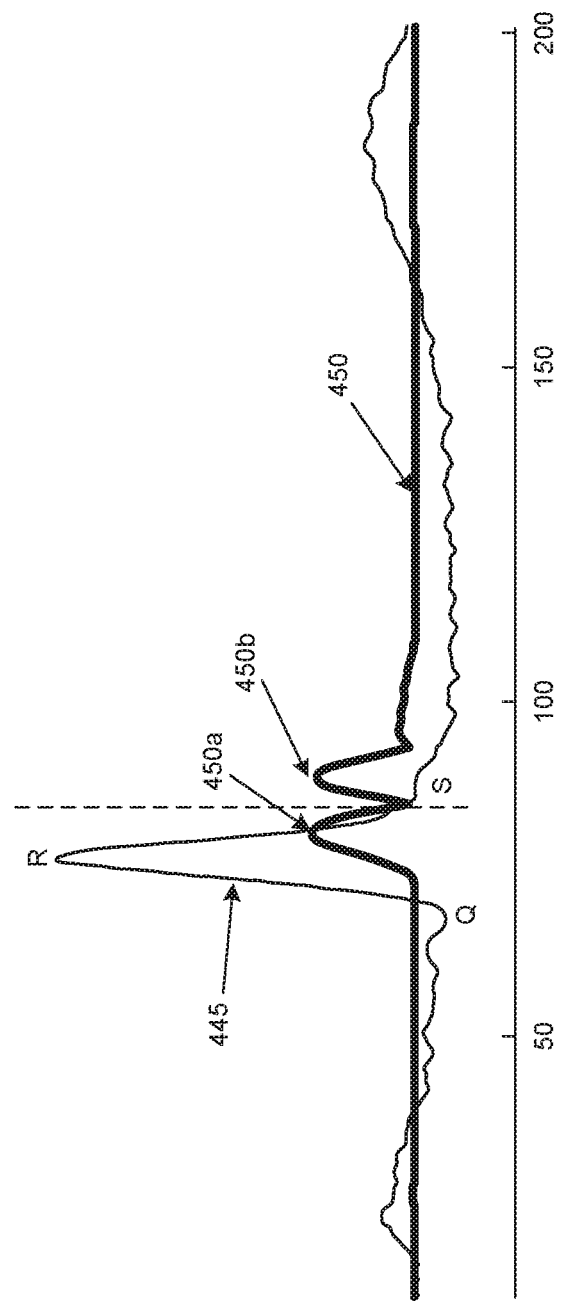
FIGS. 4H and 4I illustrate electrocardiogram signals and corresponding decomposed power signals in accordance with some embodiments.
Figure 4I:
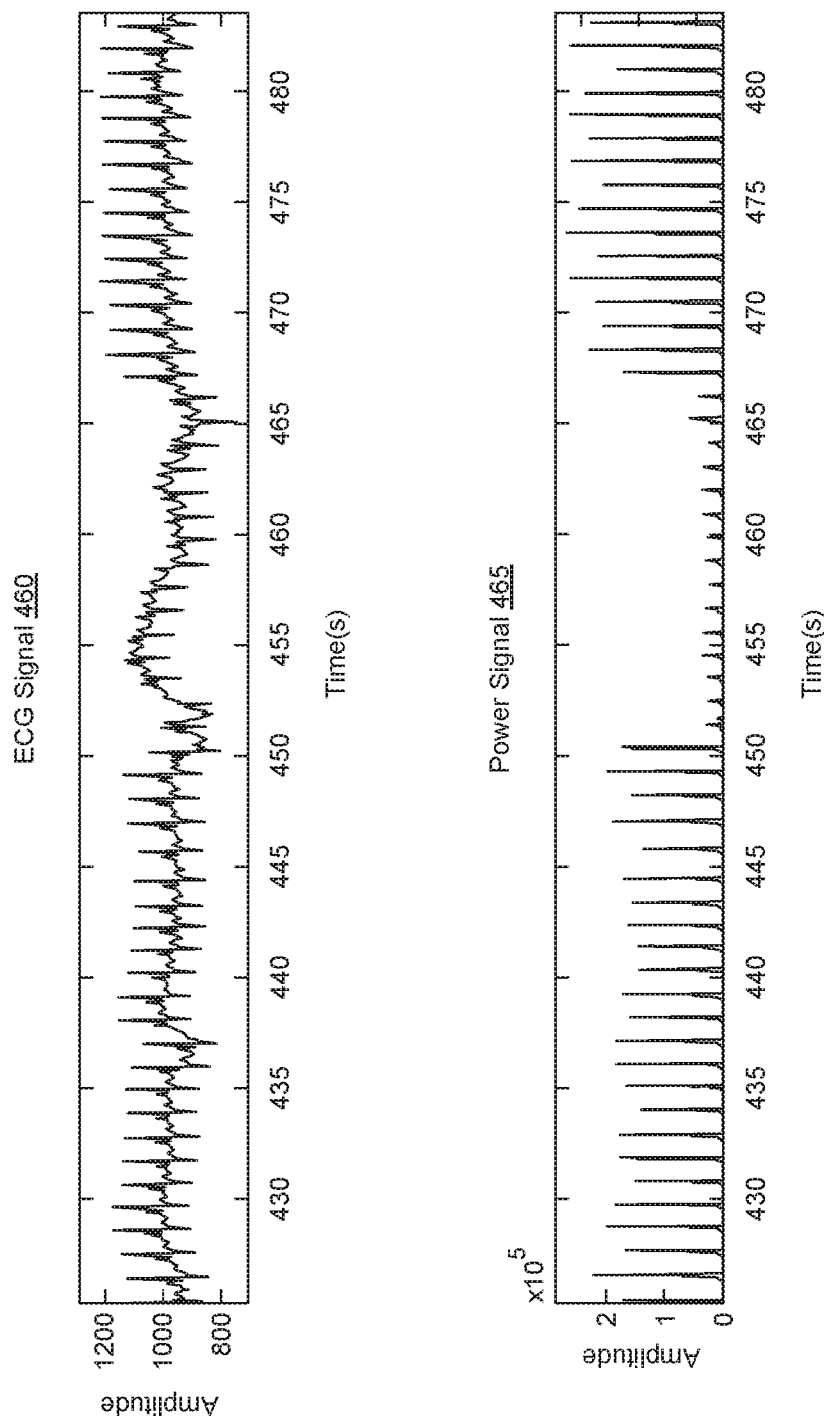

In several embodiments, the power signal includes two peaks that correspond to the rise from Q to R and the fall from R to S in the QRS complex. For example, FIG. 4H illustrates a power signal 450 that includes two peaks 450a and 450b that correspond to the rise from Q to R and the fall from R to S in the QRS complex of a corresponding electrocardiogram signal 445. FIG. 4I is another illustration that depicts an electrocardiogram signal 460 and its corresponding decomposed signal 465.

Figure 5A:
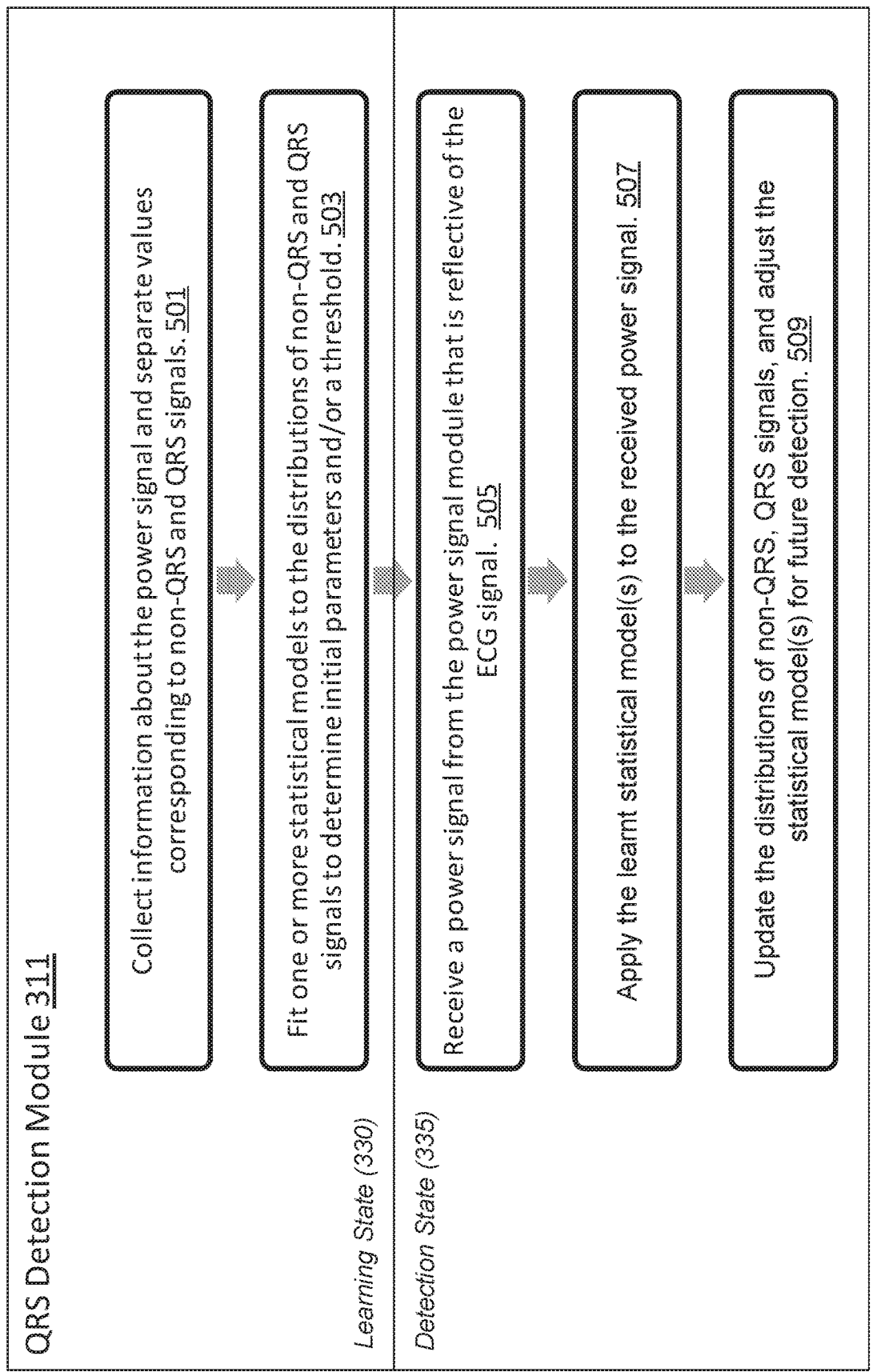
FIG. 5A is a flow diagram illustrating a method performed by a QRS Detection module of a controller in accordance with some embodiments.

In several embodiments, after generating a power signal corresponding to the received electrocardiogram signal, the QRS detection module 311 in the controller may be trained on attributes derived from the generated power signal to detect future R peaks. FIG. 5A is a flow diagram illustrating a method performed by the QRS Detection module 311 of a controller in accordance with some embodiments. At act 501, the QRS Detection module 311 collects information about the computed power signal and separates values corresponding to non-QRS and QRS signals. At act 503, the QRS Detection module 311 fits one or more models to the distribution of non-QRS and QRS signals to determine initial parameters and/or one or more threshold values. For example, during the learning state of the controller, the QRS detection module 311 of the controller selects a first portion of the generated power spectrum signal and divides it into one or more subsets comprising sub-portions of the selected portion of the generated power spectrum signal.

Figure 5B:
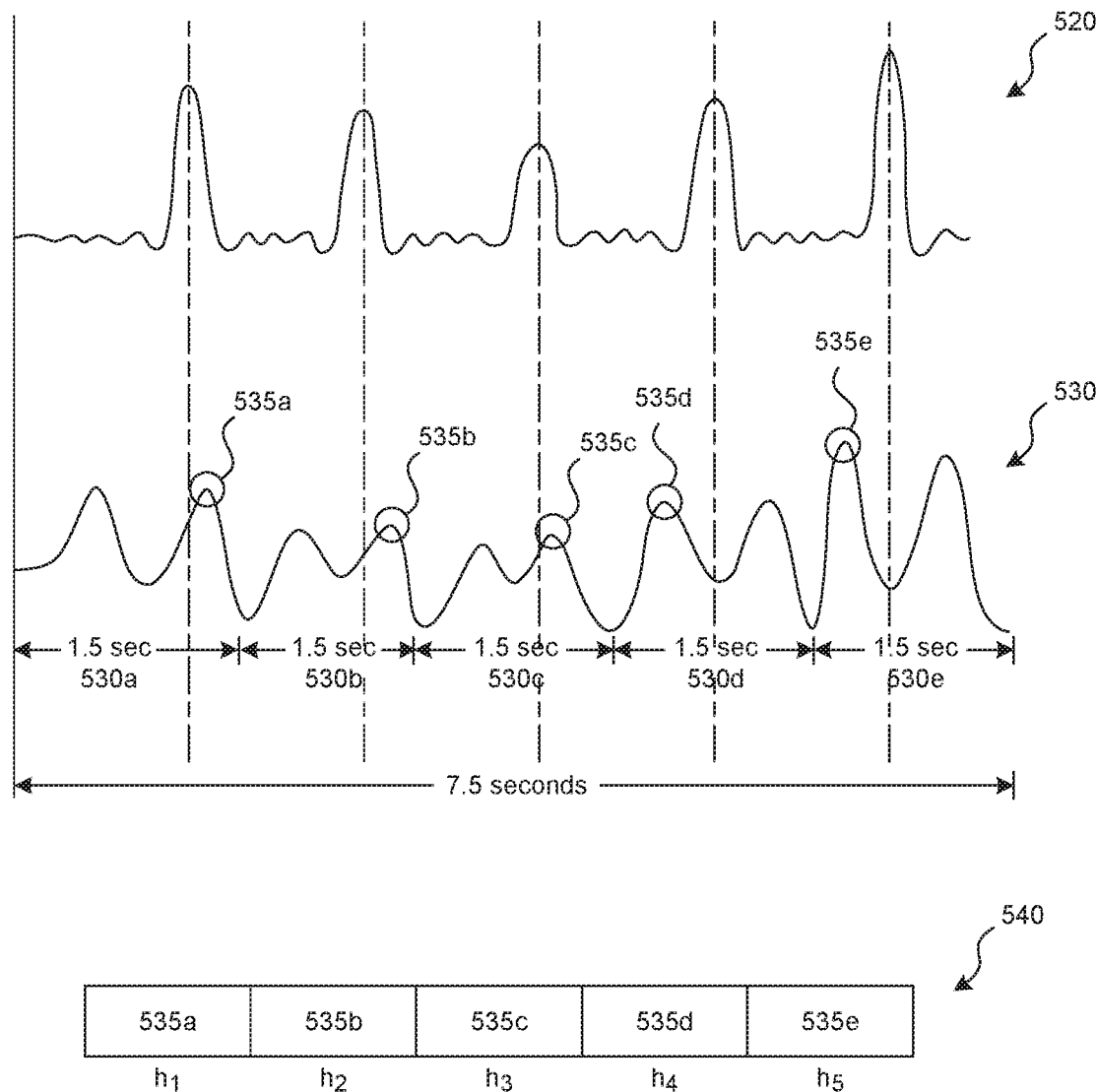
FIG. 5B illustrates the selection of h-peak values to compute threshold values in accordance with some embodiments.

As an example, illustrated in FIG. 5B, the controller selects a portion spanning 7.5 seconds of the power spectrum signal 530 corresponding to an electrocardiogram signal 520. The controller divides the power signal 530 into five subsets (530a, 530b, 530c, 530d, and 530e), each spanning 1.5 seconds. For each of these subsets, the controller computes a h-peak value of the sub-portion. In several embodiments, the controller stores the computed h-peak value of the selected portion of the power spectrum signal falling within the subset (that is, maximum h-signal value per subset). For example, the controller stores the h-peak values of the subset (535a, 535b, 535c, 535d, and 535e) in a first threshold buffer 540. The controller then computes a first adaptive threshold R-peak value based on the computed peak values stored in the first threshold buffer. For example, the controller computes a median value (or mean, weighted mean, weighted median, and so on) for the h-peak values in the threshold buffer 540 and then computes a percentage (for example, a configurable percentage of 40%) of the median value as the first adaptive threshold R-peak value for the patient. The configurable percentage can be a value within a predetermined range (for example, 20% to 27%). The configurable percentage value can be configured (or reconfigured) automatically or manually (for example, by a physician). For example, the configurable percentage value can be configured (or reconfigured) automatically using a Signal-to-Noise Ratio (SNR) of the ECG Signal. As the SNR increases, the configurable percentage value can be reduced, which leads to faster detections. On the other hand, when the patient's noise level rises to the point where it almost drowns out the R-waves, the configurable percentage value can be raised to avoid triggering the pump on noise. As another example, the configurable percentage value can be configured (or reconfigured) automatically using a measure of the R-Wave Amplitude Variability. When a patient's R-wave peak amplitude varies widely and often—as may be the case with heart failure patients with premature ventricular contractions (PVCs), bigeminy or trigeminy, or other cardiac pathologies—the controller can adjust the configurable percentage value so that it can detect both low-amplitude and high-amplitude R-waves. An example of such a measure might be the standard deviation or variance of some set of maximum h-signal peak values measured during the learning phase, or even during a separate "check-up" time period of a particular duration every so often while running in the detection phase. The controller can periodically update the values in the first threshold buffer 540 based on updated electrocardiogram signal values to then recompute the first adaptive threshold R-peak value for the patient.

In several embodiments, the controller performs an outlier detection routine, which removes outliers from the calculation of the h-peak values. In this manner, the facility addresses the problems with conventional systems, which are known to be sensitive to outliers, by implementing outlier detection at various stages in the processes carried out by the QRS detection module 311 where the h-peak values are computed. In some embodiments, an outlier may be defined as anything that falls three standard deviations from the median (or mean, or weighted mean, or weighted median, and so on) value. In some embodiments, the controller uses an approximation of the outlier for computational simplicity and to provide a more accurate estimate of the standard deviation. In some embodiments an outlier may be defined as values that are greater than $\gamma^*\text{mean(peaks)}$ where $\gamma>1$. In some embodiments, the QRS detection module 311 may only consider right-sided outliers (i.e., values significantly greater than the median).

Peak Detection State

After computing the first adaptive threshold R-peak value for the patient, the controller enters the peak detection state 335. As depicted in FIG. 5A at act 505, the QRS Detection Module 311 of the controller receives a patient's current/ most recent electrocardiogram signal (second electrocardiogram signal). Like the learning state 330, the controller in the peak detection state 335 generates a second power spectrum signal by decomposing the received second electrocardiogram signal. For example, the controller selects a first portion of the generated second power spectrum signal and divides the selected first portion of the generated second power spectrum signal into one or more second subsets comprising sub-portions of the selected first portion of the generated second power spectrum signal. For example, the controller selects a portion spanning 7.5 seconds of the second power spectrum signal and divides it into 5 subsets, each spanning 1.5 seconds. For each of these subsets, the controller computes a peak value of the sub-portion of the selected first portion of the second power spectrum signal falling within the subset (that is, a peak h-signal value per subset). In several embodiments, the controller stores the computed peak value of the subset in a second threshold buffer. The controller then computes a second adaptive threshold R-peak value based on the computed peak values stored in the second threshold buffer. For example, the controller computes a median value for the h-signal values in the second threshold buffer and then computes a percentage (for example, a configurable percentage of 40%) of the median value as the second adaptive threshold R-peak value for the patient.

At act 507, the controller applies the model(s) learnt during the learning state (for example, at act 503) to the second power spectrum signal. In several embodiments, the controller determines whether a currently received electrocardiogram signal includes a QRS complex by applying the first adaptive threshold R-peak value, the second adaptive threshold R-peak value, or both to a power signal corresponding to the currently received electrocardiogram signal. For example, in some embodiments, the presence of the QRS complex is determined when the power signal is greater than the first adaptive threshold R-peak value, the second adaptive threshold R-peak value, or both. The absence of the QRS complex is determined when the power signal is less than the threshold value(s). Since the electrocardiogram signal is a non-stationary signal whose statistical characteristics change over time, in some embodiments, approaches have been developed to make this threshold adaptive such that it changes with changing characteristics of the signal. Additionally, the facility may include other mechanisms to improve detection consistency, such as including prior information about the location of QRS, placing limits on how close adjacent QRS complexes can be in time, and improving future decisions based on past errors in detection.

Figure 6:
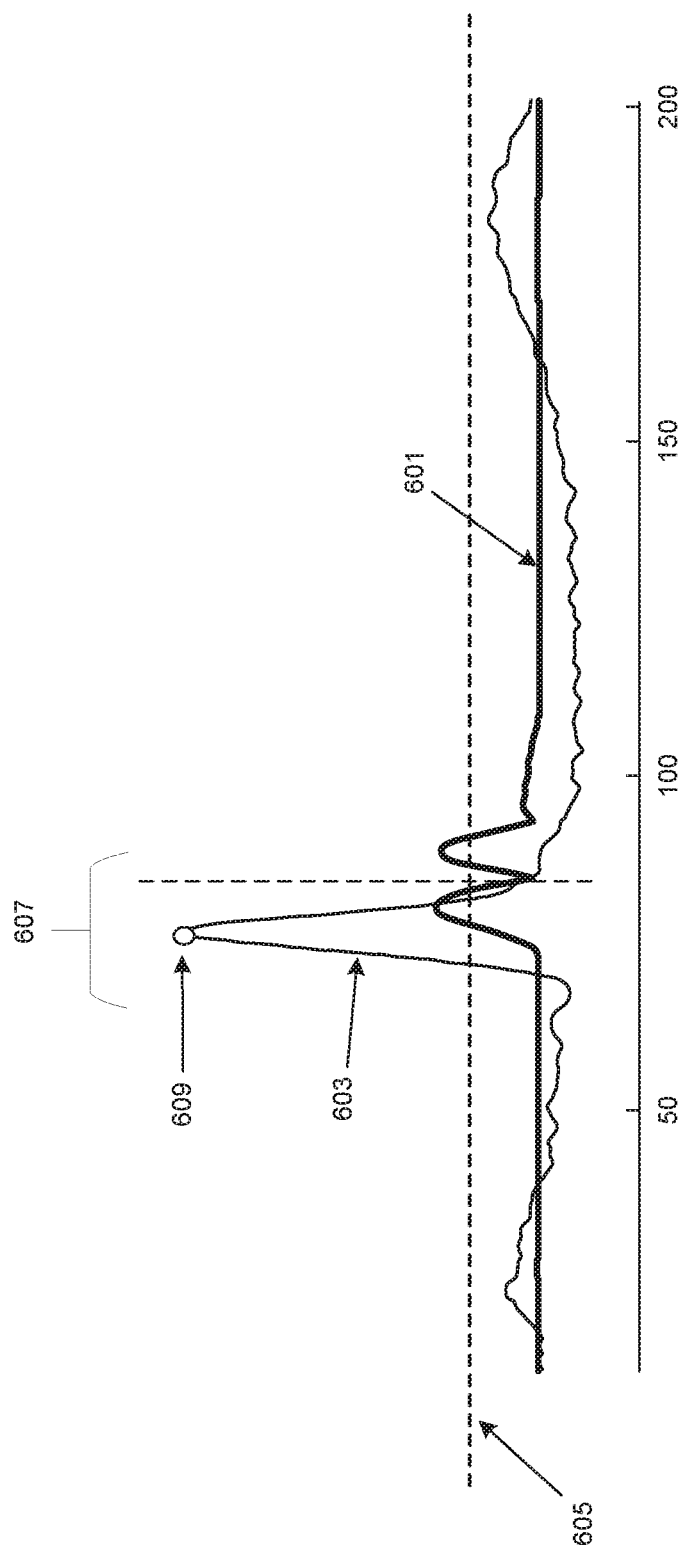
FIGS. 6 and 7 illustrate the result of applying an adaptive threshold to detect the occurrence of R peaks in accordance with some embodiments.
Figure 7:
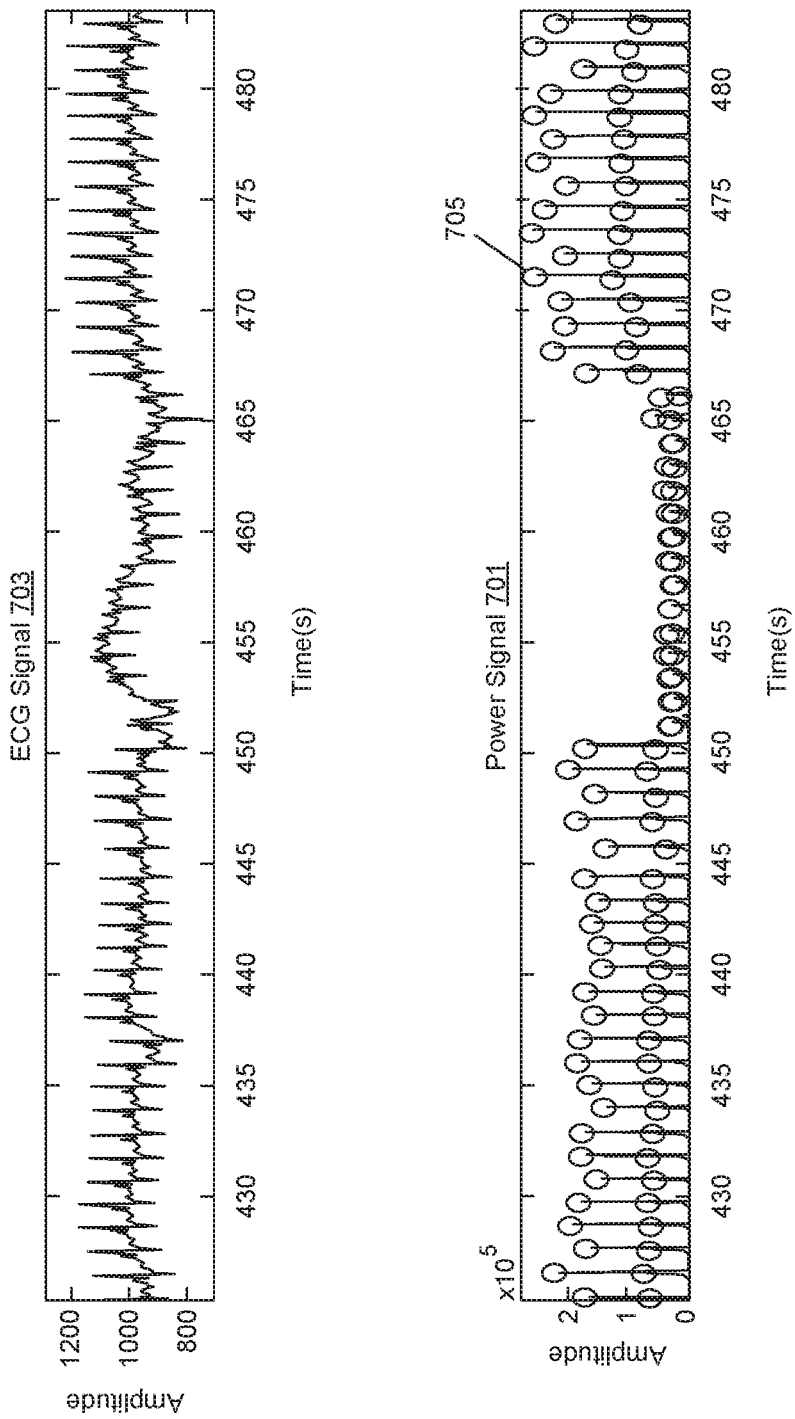

FIGS. 6 and 7 illustrate the result of applying an adaptive threshold to detect the occurrence of R peaks. For example, as illustrated in FIG. 6, a power signal 601 may be generated that is reflective of the electrocardiogram signal 603. An adaptive threshold 605 may be applied to the power signal 601 to detect a QRS complex 607 and estimate an R-peak 609. FIG. 7 similarly illustrates the result of applying an adaptive threshold to detect the occurrence of R peaks. As illustrated a power spectrum signal 701 may be generated that is reflective of the electrocardiogram signal 703. As illustrated, R-peak detections 705 may be overlaid upon the power spectrum 701.

When it is determined that the received electrocardiogram signal includes the QRS complex, QRS signals, QRS detections, R-peaks, and other data from the QRS detection module 311 may be passed to the R-to-R timing module 313. The R-to-R timing module 313 computes an R-to-R time interval value indicative of timing between two successive R-peaks in successive QRS complexes in the received second electrocardiogram signal of the patient. The R-to-R time interval value may be determined by taking the average of a buffer of the 7 most recent R-R intervals. In some embodiments, the R-to-R time interval value is calculated as the median of the 5 most recent R-R intervals. Using the median may result in superior outlier rejection of the median (versus the mean) along with the faster response of the system to rapidly changing heart rates. The controller may determine the patient's heart rate by taking the reciprocal of the calculated R-R interval and multiplying by 60 to yield a heart rate in beats per minute (BPM). The controller may also generate a prediction of timing of one or more future R-peaks based on the computed R-to-R time interval value indicative of timing between two successive R-peaks in successive QRS complexes. In several embodiments, the controller triggers an inflation of the at least one intra-aortic balloon pump based on the generated prediction of timing of the future R-peak(s).

Based on the prediction of an occurrence of a future R element, the drive unit moderator 315 of the controller 111 may be used to control the drive unit 109 of an intra-aortic balloon pump or other medical device. For example, the inflation of the balloon may be timed to the predicted occurrence of a future R element in the QRS complex.

The controller periodically updates the values in the first and/or second threshold buffers based on updated electrocardiogram signal values to then recompute the second adaptive threshold R-peak value for the patient. In several embodiments, the controller updates the first adaptive threshold R-peak value based on the second adaptive threshold R-peak value, and/or vice-versa (FIG. 5A, act 509).

In several embodiments, at least a portion of the contents of the second threshold buffer are replaced by those of the first threshold buffer (in effect resetting the adaptive threshold computations based on the learning state values). For example, after every reconfigurable time interval (such as, 30 seconds), the contents of the second threshold buffer (populated during the peak detection state) are replaced by the contents of the first threshold buffer (populated during the learning state). In several embodiments, if the controller does not detect an R wave within a certain time interval (for example, 10 seconds, 30 second, and so on), the controller declares an alarm with a code indicating a lost R wave. The lost R wave alarm can be transmitted and/or communicated (for example, as visual indicators (blinking light, flashing message, and so on), audio indicators (beeping sound, read-out of message, and so on), or any other means). When the controller declares a lost R wave alarm, it may reset to the initialization state and restart the peak detection process.

In some embodiments, the QRS detection module 311 includes one or more corrective processes. In some embodiments, the corrective processes may adapt the median metric in the presence of false negatives. In particular, the corrective process may learn from errors in detection. In some embodiments, the corrective process may include adaptive search-back, which attempts to identify the likelihood that a QRS event was incorrectly missed (false negatives) and adjusts the median metric accordingly. Assuming that the heart rate does not slow drastically from QRS to QRS event, a lack of detecting a QRS event may be an indicator that an event was potentially missed (i.e., a false negative).

The corrective process may look at one or more windows of the power signal to determine if a QRS event had been detected in the window. If no QRS event had been detected, the corrective process may look at a finite window and identify the maximum value of the power signal over that range. The corrective process may assume that the maximum value corresponded to QRS event that was missed by the QRS detection module 311 because the threshold used for detection was too high. Given this missed detection, the corrective process may incorporate the peak value associated with this missed QRS event and reduces the resulting median by a predefined percentage (e.g., 15%). This incorporation of the missed value into the median and the additional percentage reduction allows the QRS detection module 311 to quickly adapt in the presence of reductions in peak values associated with QRS events, resulting in fewer missed beats.

A similar corrective process may be used in the event of false positives. In other words, the median metric used by the QRS detection module 311 may also be adapted in the presence of false positives. In some embodiments, the corrective process may account for false positives that result from incorrect detections that have taken place directly before or after a true QRS event. Assuming that the peak value in the power signal associated with a true QRS event will have a larger peak value than those belonging to pre- or post-QRS false events, peaks that are likely to correspond to false detections are separated into two categories: pre-QRS false detections and post-QRS false detections. A pre-QRS false detection occurs when an event up to a time window (e.g., 400 ms) before the true QRS event triggers the detection logic. A time window of 400 ms is reflective of an assumed maximum heart rate of 150 bpm. Under this scenario, both the peak value associated with the pre-QRS event and the peak value associated with the QRS event will have been incorporated into the median metric, and so the QRS detection module 311 is triggering on a pre-QRS event, because the threshold is too low.

Continual incorporation of peak values associated with pre-QRS false events into the median metric will perpetuate this error. Thus, using the corrective process, if two peaks are identified within a time window of each other (e.g. 400 ms) where the second peak (i.e. the true QRS event) is greater than the first peak (i.e. the pre-QRS event), the value of the first peak is removed from the median metric and the resulting median is increased by a percentage (for example, 15%). This increase in the threshold attempts to ensure that similar false positives will not occur on subsequent events. In this manner, the corrective process may correct for pre-QRS false events.

A post-QRS false detection may occur when an event triggers the QRS detection module 311 within a time window (e.g., 400 ms) after the true QRS event. Under this scenario, the first peak (i.e. the true QRS event) will be greater than the second peak (i.e. post-QRS event). The QRS detection module 311 triggering on that second event indicates that the threshold is too low and results in a false positive. Given that incorporating the peak value associated with this post-QRS false event will likely lead to continued false positives, the value of the second peak is not incorporated into the median metric. The median metric is again increased by a percentage (for example, 15%). This increase in the threshold attempts to ensure that similar false positives will not occur on subsequent events.

The techniques described herein have several advantages over conventional methods because they are initialized quickly by approximating characteristics of QRS and non-QRS distributions rather than building them directly. Additionally, they require less memory and processing than conventional systems, due to approximating the QRS and non-QRS distributions rather than calculating them directly. Furthermore, the described techniques for the QRS detection module 311 are faster in adapting to sudden changes in the power signal.

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified.

Those skilled in the art will appreciate that the process shown in FIGS. 4B, 5A, 5B, and 8 may be altered in a variety of ways. For example, the order of the acts may be rearranged; some acts may be performed in parallel; shown acts may be omitted, or other acts may be included; a shown act may be divided into sub acts, or multiple shown acts may be combined into a single act, etc.

It will be appreciated by those skilled in the art that the above-described facility may be straightforwardly adapted or extended in various ways. While the foregoing description makes reference to particular embodiments, the scope of the invention is defined solely by the claims that follow and the elements recited therein.

What is claimed is:

1. A system for operating intra-aortic balloon pumps, the system comprising:
   at least one intra-aortic balloon pump configured to be placed in the proximity of a heart of a patient; and
   at least one controller configurably connected to the at least one intra-aortic balloon pump, wherein the at least one controller comprises at least one processor and at least one non-transitory memory, wherein the at least one controller is configured to:
     detect successive QRS complexes in an electrocardiograph (ECG) signal of the patient by generating a power signal corresponding to the ECG signal, detecting when the value of the power signal is greater than a threshold R-peak value, and associating a QRS complex with the time when the value of the power signal is greater than the threshold R-peak value;

predict the occurrence of a future R-wave in the ECG signal using the detected successive QRS complexes; and control the intra-aortic balloon pump based on the predicted occurrence of the future R-wave.

2. The system of claim 1, wherein the at least one controller is configured to inflate the intra-aortic balloon pump based on the predicted occurrence of the future R-wave.

3. The system of claim 1, wherein the at least one controller is configured to deflate the intra-aortic balloon pump based on the predicted occurrence of the future R-wave.

4. The system of claim 1, wherein the threshold R-peak value is based on a historic ECG signal of the patient.

5. The system of claim 4, wherein the at least one controller is configured to generate the historic power signal based on the historic ECG signal and wherein the threshold R-peak value is a function of two or more peak values associated with the historic power signal.

6. The system of claim 1, wherein the predicted occurrence of the future R-wave represents an amount of time from a previously detected QRS complex in the ECG signal, the amount of time being a function of the time intervals between the detected successive QRS complexes.

7. The system of claim 1, wherein the at least one controller generates the power signal by applying a transformation signal to the ECG signal.

8. The system of claim 7, wherein the transformation signal is a wavelet transformation.

9. The system of claim 1, wherein the at least one controller is further configured to:
determine if a QRS complex has not been detected within a window of time in which it is expected; and
adjust the threshold R-peak value in response to said determination.

10. The system of claim 1, wherein the at least one controller is further configured to:
determine if a detected QRS complex is a false positive; and
adjust the threshold R-peak value in response to said determination.

11. A computer implemented method for operating intra-aortic balloon pumps, the method comprising:
detecting successive QRS complexes in an electrocardiograph (ECG) signal of the patient by generating a power signal corresponding to the ECG signal, detecting when the value of the power signal is greater than a threshold R-peak value, and associating a QRS complex with the time when the value of the power signal is greater than the threshold R-peak value;
predicting the occurrence of a future R-wave in the ECG signal using the detected successive QRS complexes; and
controlling the intra-aortic balloon pump based on the predicted occurrence of the future R-wave.

12. The method of claim 11, the method further comprises one or more of:
inflating the intra-aortic balloon pump based on the predicted occurrence of the future R-wave; and
deflating the intra-aortic balloon pump based on the predicted occurrence of the future R-wave.

13. The method of claim 11, wherein the threshold R-peak value is based on a historic ECG signal of the patient.

14. The method of claim 13, further comprising generating the historic power signal based on the historic ECG signal, wherein the threshold R-peak value is a function of two or more peak values associated with the historic power signal.

15. The method of claim 11, wherein the predicted occurrence of the future R-wave represents an amount of time from a previously detected QRS complex in the ECG signal, the amount of time being a function of the time intervals between the detected successive QRS complexes.

16. The method of claim 11, further comprising generating the power signal by applying a transformation signal to the ECG signal.

17. The method of claim 16, wherein the transformation signal is a wavelet transformation.

18. The method of claim 11, further comprising:
determining one or more of:
that a QRS complex has not been detected within a window of time in which it is expected; and
that a detected QRS complex is a false positive; and
adjusting the threshold R-peak value in response to said determination.

* * * * *